United States Patent
Rubbers

(10) Patent No.: US 7,035,776 B2
(45) Date of Patent: Apr. 25, 2006

(54) LOW NOISE TO SIGNAL EVALUATION

(75) Inventor: Philippe Rubbers, Gauteng (ZA)

(73) Assignee: Eskom, Gauteng (ZA)

(*) Notice: Subject to any disclaimer, the term of this patent is extended or adjusted under 35 U.S.C. 154(b) by 46 days.

(21) Appl. No.: 10/258,646

(22) PCT Filed: Apr. 25, 2001

(86) PCT No.: PCT/IB01/00685
§ 371 (c)(1),
(2), (4) Date: Feb. 28, 2003

(87) PCT Pub. No.: WO01/81948
PCT Pub. Date: Nov. 1, 2001

(65) Prior Publication Data
US 2003/0182089 A1 Sep. 25, 2003

(30) Foreign Application Priority Data
Apr. 25, 2000 (ZA) .......................... 2000/2040

(51) Int. Cl.
G06F 17/10 (2006.01)
H04B 15/00 (2006.01)

(52) U.S. Cl. ................. 702/190; 702/106; 702/197; 375/350; 708/300

(58) Field of Classification Search ........... 324/76.12, 324/76.29, 76.53, 76.19, 76.68, 613; 375/350; 708/300; 702/69, 72, 73, 106, 189, 190, 197
See application file for complete search history.

(56) References Cited

U.S. PATENT DOCUMENTS

| | | | |
|---|---|---|---|
| 4,676,250 A | | 6/1987 | Barnes |
| 4,751,846 A | | 6/1988 | Dousse |
| 4,837,578 A | | 6/1989 | Gammell |
| 4,896,285 A | * | 1/1990 | Ishikawa et al. ............ 708/300 |
| 5,187,687 A | | 2/1993 | Burckhardt et al. |
| 5,253,271 A | * | 10/1993 | Montgomery ................ 375/295 |
| 5,384,856 A | * | 1/1995 | Kyouno et al. .............. 381/103 |
| 5,445,156 A | | 8/1995 | Daft et al. |
| 5,448,596 A | * | 9/1995 | Ezran et al. ................ 375/350 |
| 5,891,038 A | | 4/1999 | Seyed-Bolorforosh et al. |
| 6,097,328 A | * | 8/2000 | Frankot ..................... 342/25 C |
| 6,324,290 B1 | * | 11/2001 | Murakami et al. ............ 381/92 |
| 6,351,451 B1 | * | 2/2002 | Butash ....................... 370/210 |
| 6,470,365 B1 | * | 10/2002 | Rahman et al. ............. 708/313 |
| 6,717,991 B1 | * | 4/2004 | Gustafsson et al. ......... 375/285 |
| 6,731,710 B1 | * | 5/2004 | Genossar et al. ........... 375/362 |
| 2005/0025222 A1 | * | 2/2005 | Underbrink et al. ........ 375/141 |

FOREIGN PATENT DOCUMENTS

JP          07225273 A    *    8/1995

OTHER PUBLICATIONS

International Search Report for PCT/IB 01/00685 of Nov. 26, 2001.
"Utility of Split–Spectrum Processing in Ultrasonic Nondestructive Evaluation", J. L. Rose, P. Karpur and V. L. Newhouse, *The American Society for Nondestructive Testing*, Materials Evaluation/46/Jan. 1986, pp. 114–122.

* cited by examiner

Primary Examiner—Marc S. Hoff
Assistant Examiner—Paul Kim
(74) Attorney, Agent, or Firm—Fitch, Even, Tabin & Flannery

(57) ABSTRACT

The invention provides for improved signal to noise ratios in evaluation techniques. This is done by acquiring a signal, processing it to obtain a complex form thereof, obtaining a filtering factor from the complex form and processing the acquired signal with the filtering factor. The signal may be a returned ultrasonic, radar or sonar signal which may be reflected from a suitably sharp pulse. In particular, the invention may he used to evaluate articles to detect defects therein. In a preferred form, the complex form is filtered with a number of complex filters and the phases of the complex filtered signals determined. These phases are then used to provide the filtering factor.

20 Claims, 5 Drawing Sheets

LOW NOISE TO SIGNAL EVALUATION

BACKGROUND OF THE INVENTION

Field of the Invention

This invention relates to evaluation methods and systems. In one particular form it relates to a method and system for ultrasonic non-destructive evaluation of an article.

BRIEF SUMMARY OF THE INVENTION

According to the invention there is provided an evaluation method, which includes acquiring a signal;

processing the acquired signal to obtain a complex form thereof; obtaining a filtering factor from the complex form; and processing the acquired signal with the filtering factor.

Further according to the invention, there is provided an evaluation system, which includes an acquisition means for acquiring a signal;

a complex form obtaining means for processing the acquired signal to obtain a complex form thereof;

a filtering factor providing means for providing a filtering factor from the complex form; and a filter processing means for processing the acquired signal with the filtering factor.

The acquired signal may have coherent wideband properties. It may, in one embodiment, be a returned signal resulting from a test signal, which may be an excitation pulse. The signals may be ultrasonic, sonar or radar in nature. The excitation pulse may be suitably sharp, with suitably fast rise and fall times.

A causal signal may be derived from the acquired signal and the causal signal and the acquired signal may be combined to provide the complex form thereof. The system may thus include a deriving and combining means for deriving the causal signal from the acquired signal and for combining the causal signal and the acquired signal to provide the complex form thereof.

The causal signal may be derived by means of a Hilbert Transform. Instead, as those skilled in the art will appreciate, one may divide the differentiated acquired signal by the component frequencies thereof. Further, as those skilled in the art will appreciate, the Hilbert transform can be implemented by a) performing a Fast Fourier Transform (FFT), multiplying by $\sqrt{-1}$ for all frequencies from 0 to half the sampling rate and $-\sqrt{-1}$ for all the frequencies from half the sampling rate to the full sampling rate, and an Inverse Fast Fourier Transform (IFFT); or b) performing an FFT, multiplying by $2*\sqrt{-1}$ for all frequencies from 0 to half the sampling rate and making all frequency values from half the sampling rate to the full sampling rate equal to zero, and an IFFT.

The acquired signal may be converted from an analogue form to a digital form by suitable AID converters.

The complex form signal may be filtered with a number of complex filters and the complex filtered signals may be evaluated to find their phases. The phases from the complex filters may then be compared and used to determine the filtering factor. The acquired signal may then be multiplied by the filtering factor to obtain an evaluation signal.

As indicated above, the invention may be used to evaluate an article in a non-destructive manner.

Those skilled in the art will appreciate further that the acquired signal has a potential energy component and a kinetic energy component and that the returned signal that is detected represents the potential energy component of the returned wave. The kinetic energy component can be represented by the causal signal.

Discrete devices may be provided to perform the various operations described above. Instead a suitably programmed computer may be used to perform the various operations.

By means of the invention the signal to noise ratio of the evaluation signal is improved.

BRIEF DESCRIPTION OF THE DRAWINGS

The invention is now described, by way of an example, with reference to the accompanying drawings, in which.

DETAILED DESCRIPTION OF THE INVENTION

Figure 1:
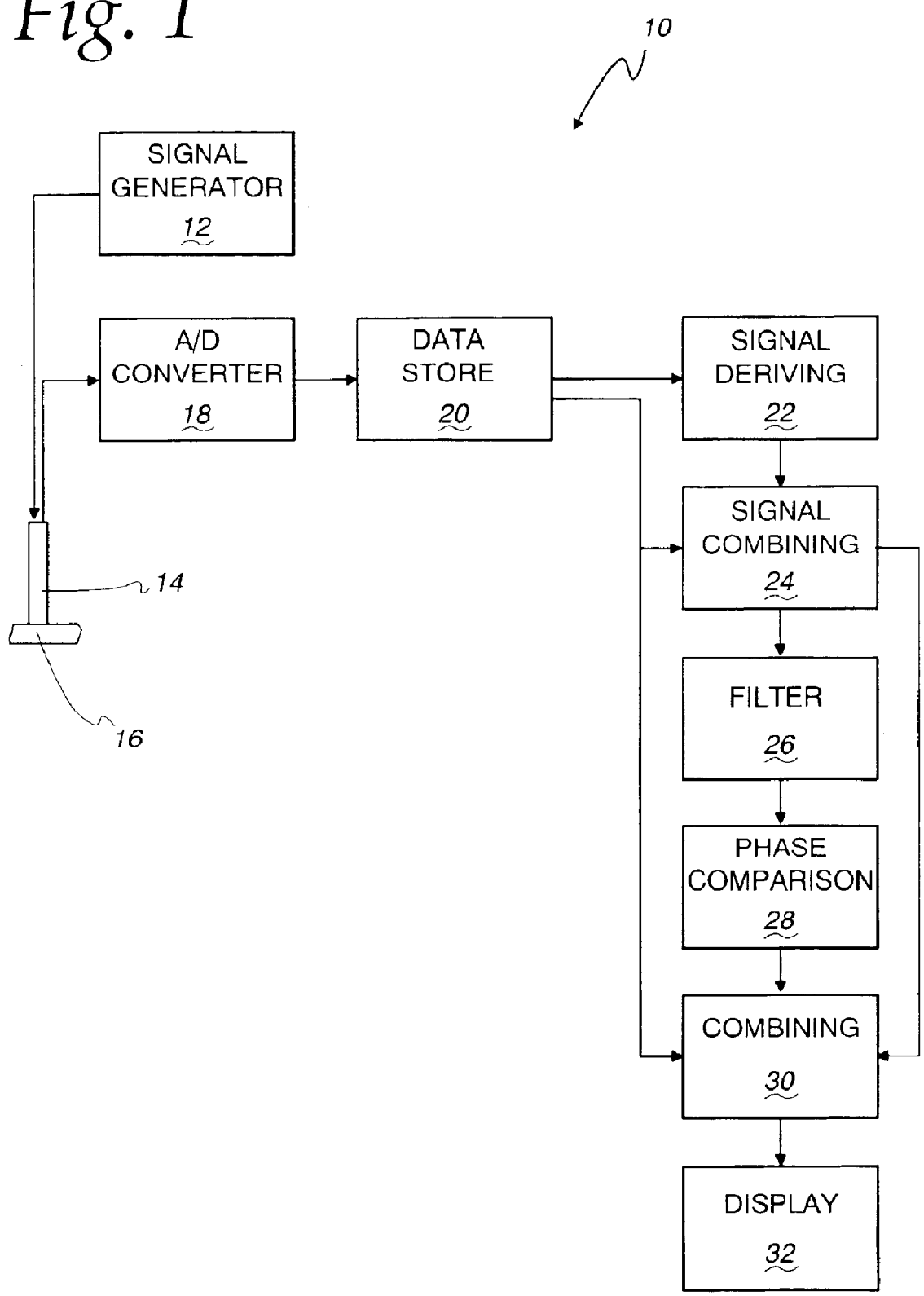
FIG. 1 shows a schematic block diagram of a system for evaluating an article ultrasonically in accordance with the invention.

Referring now to FIG. 1, a system for evaluating an article is designated generally by reference numeral 10. The system 10 has a signal generator 12 which supplies a test signal to a transmitter 14 which, in turn, applies the test signal to an article 16 which is to be evaluated to determine if it has any reflectors of interest. The receiver 14 also receives a reflected signal from the article and supplies it to an analogue to digital ("A/D") converter 18. The AID converter 18 is connected to a store 20 which stores the digital data. As indicated above, the data stored is representative of the original signal or the real component of the complex signal.

The system further has a causal signal deriving device 22 which derives the causal signal of the reflected signal. As discussed above, the causal signal deriving device 22 also supplies a signal which is representative of the imaginary component of the complex waveform.

The two signals are combined in a device 24 which provides the total signal and the waveform in complex form. The output of the device 24 is filtered by a filter device 26 which supplies a number of complex filtered signals whose phase is then compared in a phase comparison device to generate a filtering factor 28 which then combines with either the original signal or the magnitude waveform in the combining device 30 to supply an evaluation signal which is made available to a display 32, which can then be used to assess if the article 16 has any reflectors of interest.

The signal generator 12 may supply a signal to the transmitter to generate a broad band signal with components in a number of frequencies. The signal generator is a Panametrics 5073 PR unit which supplies a pulse with a rising edge of 2 ns, a falling edge of 10 ns and a peak voltage of 700V, and hence a sufficiently broad band signal.

The transmitter 14 has a wide bandwidth in the required frequency range. For austenitic castings, this could be in the 500 KHz to 2.5 MHz range. The transmitter 14 is a Karl Deutsch model S24 HB 0.5–4 probe, which has a range of 500 KHz to 4.5 MHz.

The A/D converter 18 has a sampling rate of 250 MHz with 10 bits per sample and is a Tektronix TDS 754C 4 channel, 500 MHz, 2 GS/s device.

The causal signal deriving device 22, the device 24, the filter device 26 and the phase comparison device 28 and the combining device 30 were all implemented digitally by means of a suitably programmed PC.

Figure 2:
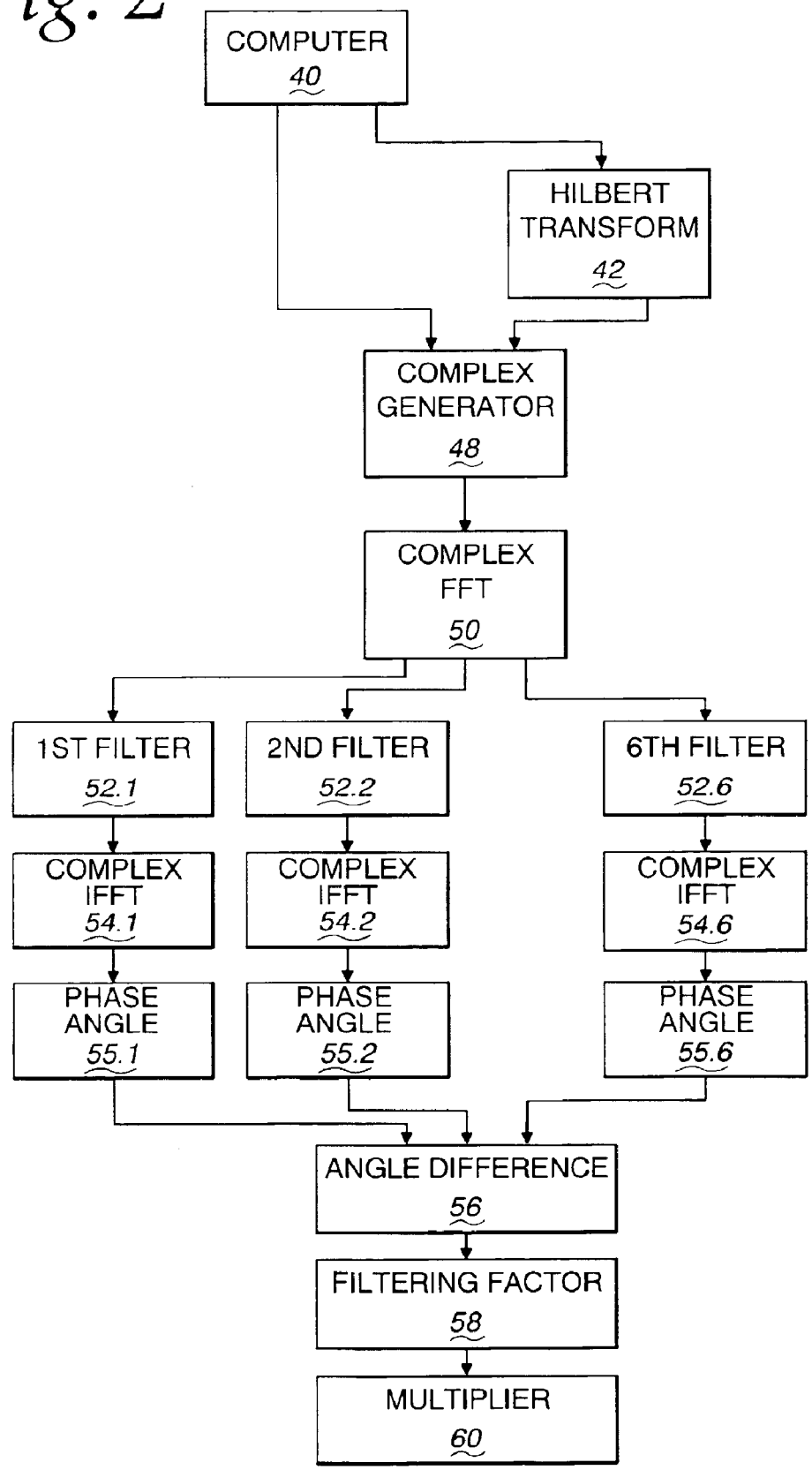
FIG. 2 shows a flow chart indicating the operational steps of the computing device.

Reference is now made to FIG. 2 which illustrates the processing steps followed by the causal signal deriving device 22, the device 24, the filter device 26, the phase comparison device 28, and the combining device 30, as implemented by the programmed computer. As indicated at 40, the digital signals supplied by the A/D converter 18 are transferred to the computer. The computer then performs a Hilbert transform on the data at 42 to get the causal signal or imaginary component. The original data and the data resulting from step 42 are combined, at 48, to generate a set of complex numbers, with the real part being the original signal and the imaginary part being the causal signal.

A complex FFT is then performed on the data resulting from step 48, at 50. The resulting complex data is then filtered, in a computational manner. Thus, the complex specifications of a desired number of suitable filters are provided and these specifications are subjected to FFT's, the results of which are stored in the computer. In the particular example, six filters are used. The complex FFT provided at 50 is then processed with each of the six transformed filter specifications. Thus, the complex FFT is multiplied by the FFT of a first filter, at 52.1 and a complex IFFT performed on the result, at 54.1; the complex FFT is multiplied by the FFT of a second filter, at 52.2 and a complex IFFT performed on the result, at 54.2; and so on with the complex FFT being multiplied by the FFT of the sixth filter, at 52.6 and a complex IFFT performed on the result, at 54.1 to 54.6. The phase angle is then obtained for each filtered signal at 55.1 to 55.6. The angles are sorted and the largest difference found, at 56. A filtering factor is then determined, at 58, using suitable lower and upper threshold values and the test criteria discussed above. Finally, the original waveform is multiplied with the filtering factor, at 60.

Figure 3:
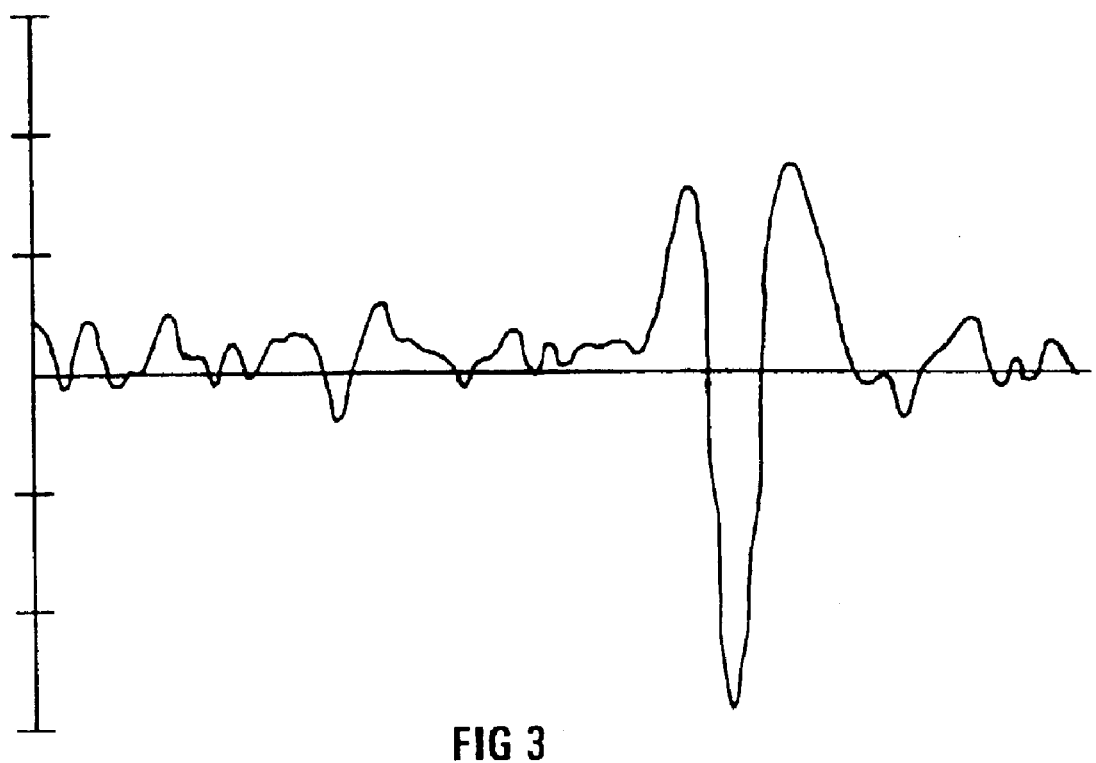
FIG. 3 shows the waveform of an acquired signal supplied by an analogue to digital converter of the system.
Figure 4:
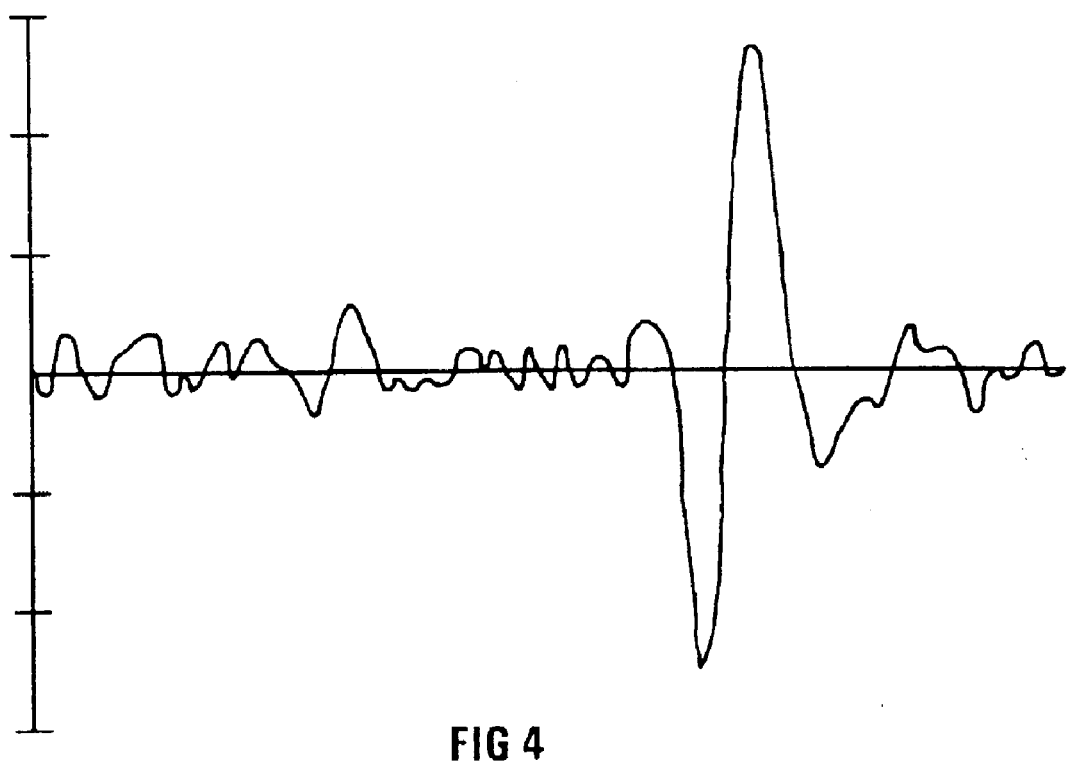
FIG. 4 shows the waveform of a derived signal supplied by a causal signal deriving device of the system.
Figure 5:
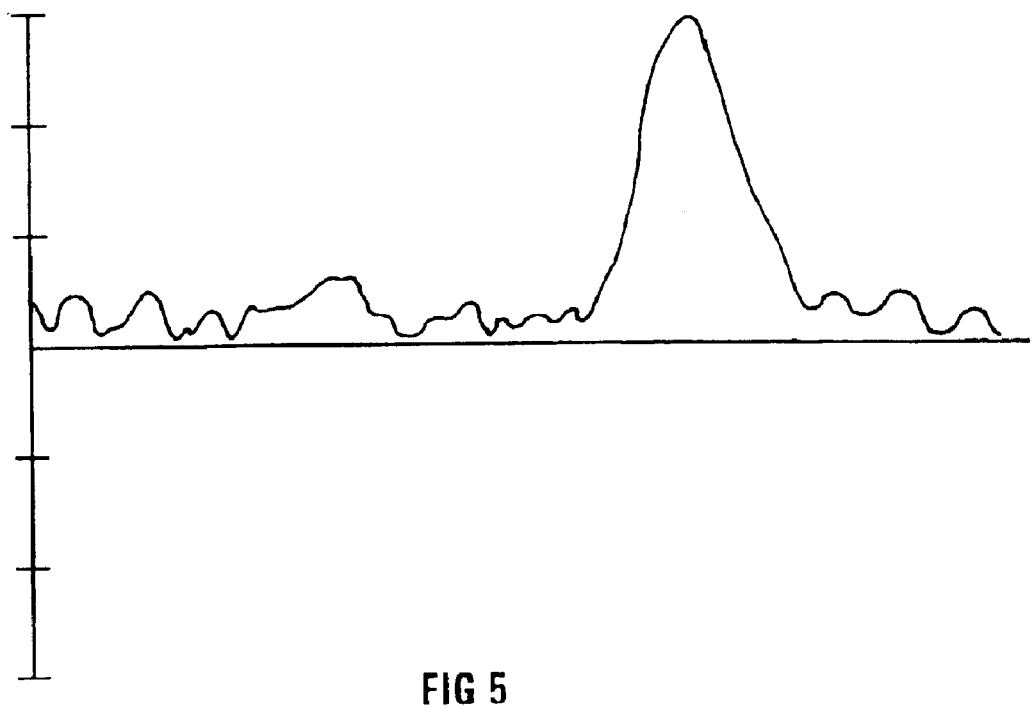
FIG. 5 shows the waveform of a total magnitude or envelope waveform supplied by a total signal deriving device of the system.

A plate of austenitic steel was evaluated by means of the invention. The plate was 79 mm thick and a hole was drilled therein. The hole had a depth of 11 mm and was 5 mm in diameter. The plate was subjected to radiography examination which revealed that it had no significant defects. The data provided by the A/D converter generated the waveform shown in FIG. 3, which represents the real part of the total signal. The causal signal as supplied at step 42 which represents the signal supplied by the causal signal deriving device, provided the waveform shown in FIG. 4. The combination of these two signals gives a complex signal. FIG. 5 represents the amplitude of the complex signal supplied by the total signal deriving device, as provided at step 48.

Figure 7:
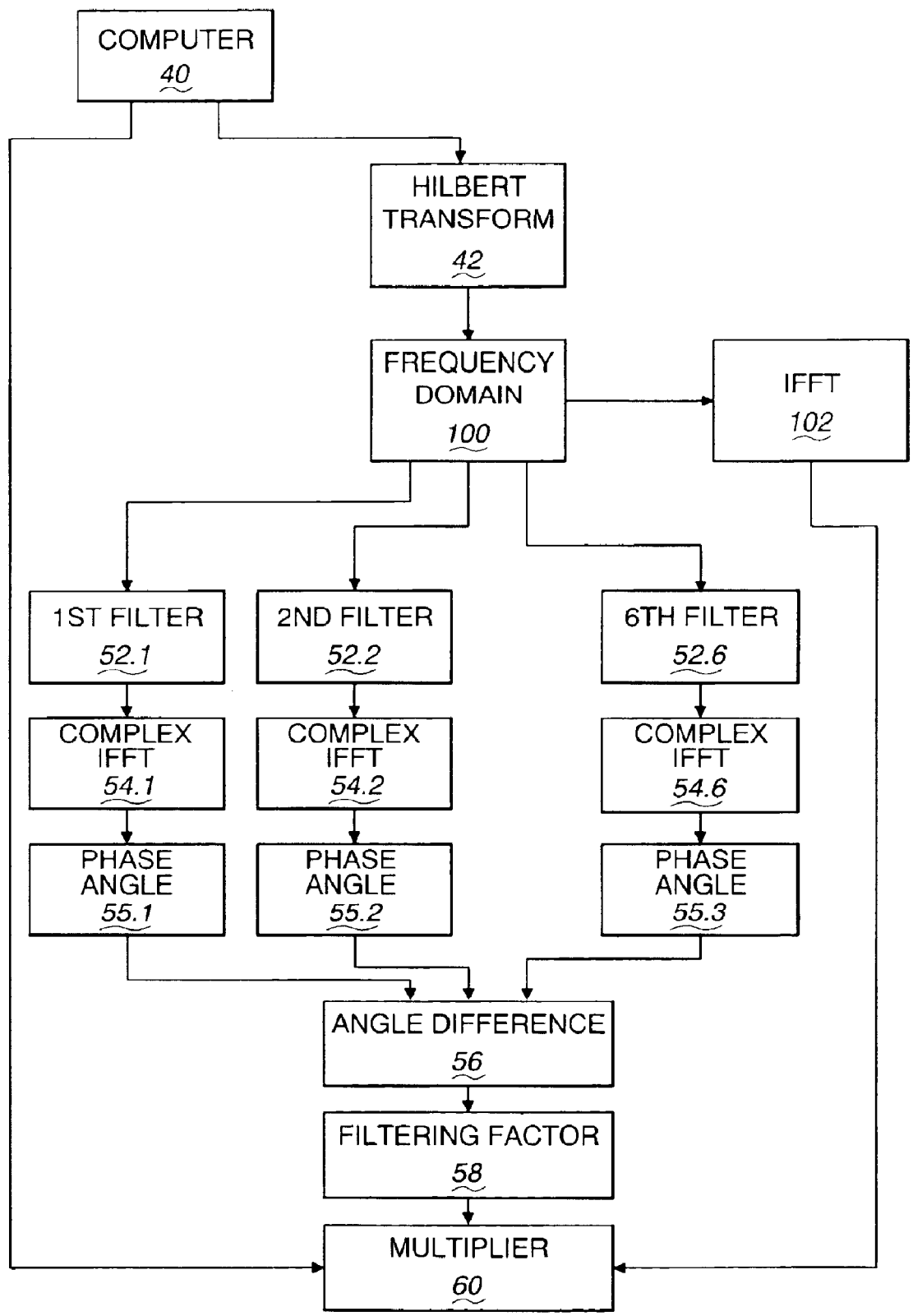
FIG. 7 shows a flow chart of a further embodiment of the invention.

Referring now to FIG. 7, the processing steps for a further embodiment of the invention, in which optimisations are achieved, and the filtered signal envelope is obtained are illustrated. Several of the steps are similar to those described above with reference to FIG. 2 and are similarly numbered.

Thus, at 40, the digital signals supplied by the A/D converter 18 are transferred to the computer. The computer then combines the Hilbert transform with the filter by performing an FFT on the data at 42, which is multiplied by $\sqrt{-1}$ to get the imaginary component, which is combined with the real part to give a complex signal, in the frequency domain, at 100. An IFFT is performed at 102 to provide the total signal for the purpose of obtaining the signal envelope.

The complex signal in the frequency domain is then filtered by various filters as numbered in FIG. 2.

Figure 6:
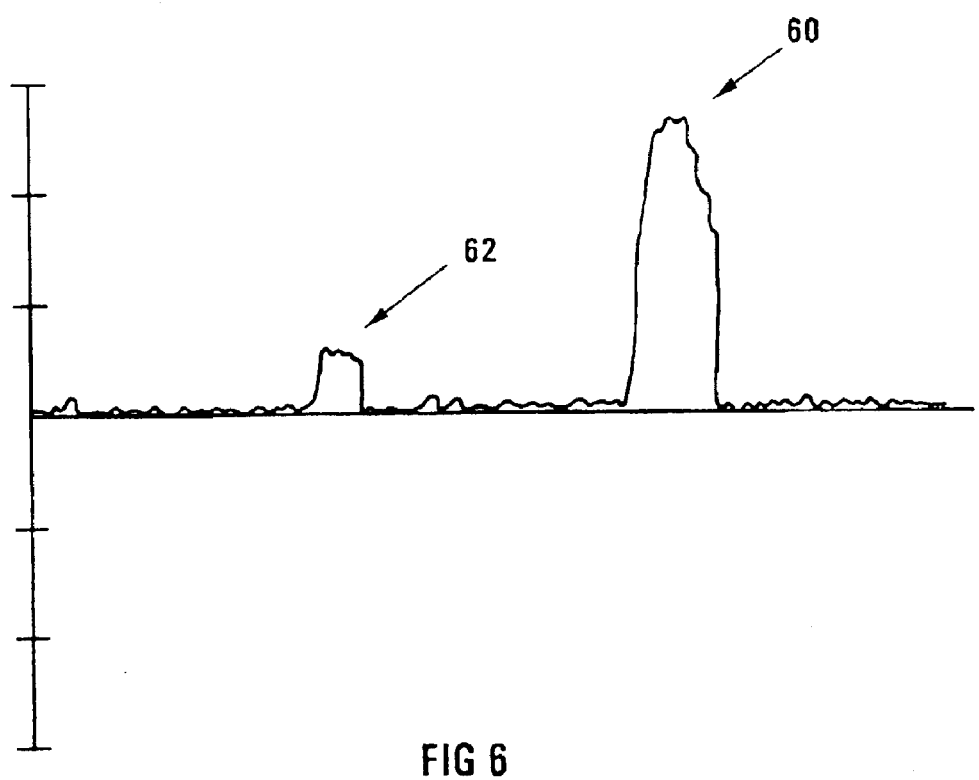
FIG. 6 shows the filtered envelope waveform supplied by a filtering and combining device of the system.

The Filtering factor can be multiplied by either the original signal, at 40, or by the signal envelope at 102 to obtain either the final filtered signal as shown in FIG. 6. The signal provided after combining the filter with the magnitude obtained at 102 is shown in FIG. 6. Two clear spikes 60 and 62 are visible. Spike 60 shows the end surface of the plate and spike 62 the hole.

What is claimed is:

1. An evaluation method for improving signal to noise ratios of broadband signals in non-destructive evaluation of materials, which includes acquiring a returned signal from a test signal;

processing the acquired signal to obtain a complex form thereof;

filtering the complex form signal with more than one complex form filter, to provide a set of complex filtered signals;

comparing the phases of the set of complex filtered signals;

obtaining a filtering factor from the comparison; and processing the acquired signal with the filtering factor.

2. The method claimed in claim 1, in which the acquired signal has coherent broadband properties.

3. The method claimed in claim 1, which includes deriving a causal signal from the acquired signal and combining the causal signal and the acquired signal to provide the complex form thereof.

4. The method claimed in claim 3, in which the causal signal is derived by means of a Hilbert transform.

5. The method claimed in claim 1, in which the acquired signal is converted from an analogue form to a digital form.

6. The method claimed in claim 1, in which the phase angles of the complex filtered signals are determined.

7. The method claimed in claim 1, in which the filtering factor is multiplied with the acquired signal to obtain an evaluation signal.

8. The method claimed in claim 7, in which the filtering factor is multiplied with the amplitude of the complex form of the acquired signal to obtain an evaluation signal.

9. The method claimed in claim 1, in which the acquired signal is an ultrasonic signal.

10. The method claimed in claim 1, in which the acquired signal is a sonar signal.

11. The method claimed in claim 1, in which the acquired signal is a radar signal.

12. The method claimed in claim 1, in which the test signal is an excitation pulse.

13. An evaluation system for improving signal to noise ratios of broadband signals in non-destructive evaluation of materials, which includes an acquisition means for acquiring a returned signal from a test signal;

a complex form obtaining means adapted to process the acquired signal to obtain the complex form thereof;

a filtering means adapted to filter the complex form signal with more than one complex form filter and to provide a set of complex filtered signals;

a comparison means for comparing the phases of the set of complex filtered signals;

a filtering factor providing means adapted to provide a filtering factor from the comparison; and a filter processing means adapted to process the acquired signal with the filtering factor.

14. The system claimed in claim 13, in which the acquired signal has coherent broadband properties.

15. The system claimed in claim 13, which includes a deriving and combining means adapted to derive a causal signal from the acquired signal and for combining the causal signal and the acquired signal to provide a complex form thereof.

16. The system claimed in claim 15, in which the deriving and combining means includes a frequency domain transform.

17. The system claimed in claim 13, which includes an analogue to digital converter for converting the acquired signal from an analogue form to a digital form.

18. The system claimed in claim 13, which includes a phase angle determining means adapted to determine the phase angles of the complex filtered signals.

19. The system claimed in claim 13, in which the filter processing means multiplies the filtering factor with the acquired signal.

20. The system claimed in claim 19, in which the filter processing means multiplies the filtering factor with the amplitude of the complex form of the acquired signal.

* * * * *